(12) United States Patent
Lee

(10) Patent No.: US 11,266,854 B2
(45) Date of Patent: Mar. 8, 2022

(54) LASER BEAM DEVICE AND LASER BEAM HAND PIECE HAVING SAME

(71) Applicant: LUTRONIC CORPORATION, Goyang (KR)

(72) Inventor: Hee Chui Lee, Goyang (KR)

(73) Assignee: LUTRONIC CORPORATION, Goyang (KR)

( * ) Notice: Subject to any disclaimer, the term of this patent is extended or adjusted under 35 U.S.C. 154(b) by 361 days.

(21) Appl. No.: 16/097,564

(22) PCT Filed: Apr. 28, 2017

(86) PCT No.: PCT/KR2017/004550
§ 371 (c)(1),
(2) Date: Oct. 29, 2018

(87) PCT Pub. No.: WO2017/188775
PCT Pub. Date: Nov. 2, 2017

(65) Prior Publication Data
US 2019/0160302 A1 May 30, 2019

(30) Foreign Application Priority Data
Apr. 29, 2016 (KR) .......... 10-2016-0053056

(51) Int. Cl.
*A61N 5/06* (2006.01)
*A61N 5/067* (2006.01)
*A61N 5/073* (2006.01)

(52) U.S. Cl.
CPC .......... *A61N 5/0616* (2013.01); *A61N 5/067* (2021.08); *A61N 2005/063* (2013.01); *A61N 2005/0652* (2013.01); *A61N 2005/073* (2013.01)

(58) Field of Classification Search
CPC .......... A61N 5/0616; A61N 2005/063; A61N 2005/0652; A61N 2005/067; A61N 2005/073
See application file for complete search history.

(56) References Cited

U.S. PATENT DOCUMENTS

| 4,454,882 | A | * | 6/1984 | Takano | ............ | A61B 18/20 |
| | | | | | | 219/121.83 |
| 5,305,759 | A | * | 4/1994 | Kaneko | ............ | A61B 5/0059 |
| | | | | | | 356/318 |

(Continued)

FOREIGN PATENT DOCUMENTS

| KR | 10-2013-0118340 A | 10/2013 |
| KR | 10-2014-0144304 A | 12/2014 |

(Continued)

OTHER PUBLICATIONS

International Search Report for Application No. PCT/KR2017/004550, dated Aug. 8, 2017.

*Primary Examiner* — Lynsey C Eiseman
*Assistant Examiner* — Amanda L Steinberg

(57) ABSTRACT

The present invention relates to a laser beam device and a laser beam hand piece having same, the laser beam device outputting a laser beam that is polarized and has high output energy. The laser beam device, according to the present invention, comprises: a light source unit emitting a pumping light; a first optical unit generating a laser beam that is polarized by being pumped by the pumping light provided from the light source unit; and a second optical unit amplifying the polarized laser beam provided from the first optical unit. Accordingly, a compact structure and the outputting of a polarized laser beam having amplified output energy may be enabled, and thus the size and manufacturing costs of the laser beam device and the laser beam hand piece having same may be reduced.

18 Claims, 6 Drawing Sheets

(56) References Cited

U.S. PATENT DOCUMENTS

| | | | | |
|---|---|---|---|---|
| 5,394,413 | A * | 2/1995 | Zayhowski | G01N 21/63 |
| | | | | 372/10 |
| 10,622,780 | B2 * | 4/2020 | Shang | H01S 3/0071 |
| 2003/0216720 | A1 * | 11/2003 | Sinofsky | A61B 18/22 |
| | | | | 606/11 |
| 2006/0171429 | A1 * | 8/2006 | Seitel | H01S 3/1083 |
| | | | | 372/10 |
| 2008/0082089 | A1 * | 4/2008 | Jones | A61B 18/22 |
| | | | | 606/9 |
| 2013/0041309 | A1 * | 2/2013 | Siegel | A61B 18/203 |
| | | | | 604/20 |
| 2014/0321484 | A1 * | 10/2014 | Sierra | H01S 3/094076 |
| | | | | 372/18 |

FOREIGN PATENT DOCUMENTS

| | | | |
|---|---|---|---|
| KR | 10-2015-0120927 A | 10/2015 | |
| KR | 10-2015-0130216 A | 11/2015 | |
| KR | 101610689 B1 | 4/2016 | |
| WO | 2012061761 A2 | 5/2012 | |
| WO | 2013158299 A1 | 10/2013 | |
| WO | WO-2019245937 A1 * | 12/2019 | ............ H01S 3/0071 |

* cited by examiner

LASER BEAM DEVICE AND LASER BEAM HAND PIECE HAVING SAME

CROSS-REFERENCE TO RELATED APPLICATIONS

The present specification is a U.S. National Stage of International Patent Application No. PCT/KR2017/004550 filed Apr. 28, 2017, which claims priority to and the benefit of Korean Patent Application No. 10-2016-0053056 filed in the Korean Intellectual Property Office on Apr. 29, 2016, the entire contents of which are incorporated herein by reference.

TECHNICAL FIELD

The present invention relates to a laser beam device and a laser beam hand piece having the same, and more particularly, to a laser beam device and a laser beam hand piece having the same for generating and emitting a medical laser beam.

BACKGROUND ART

A laser beam device has three excellent characteristics including monochromatic, coherence, and collimation as compared with general nature light and light emitted from a lamp.

The laser beam has excellent characteristics of monochromatic, coherence, and collimation to have been widely used in various industrial fields, and usability of the laser beam has been increased. For example, the laser beam device has been increasingly used in various industrial fields such as a metal industry, a construction industry, a shipbuilding industry and a medical industry. In particular, the laser beam has been used in various human tissues such as skin and eyeball in a medical field according to increased efficiency of the laser beam.

Here, a wavelength band, a pulse width, and output energy of the laser beam used in various human tissues are selectively used according to a use purpose and a polarized laser beam is widely used for the medical purpose. For example, a laser beam used for skin cure or improvement purpose is gripped and used by a practitioner in a laser beam hand piece scheme.

Meanwhile, the laser beam hand piece includes a hand piece generally gripped by a practitioner, a light source such as a laser diode connected to the hand piece, and an optical means received in the hand piece to optically process a laser beam generated from the light source to emit the laser beam to an outside.

However, a polarizing means for polarizing a laser beam provided from the light source should be included in order to be used for a medical purpose used in an existing laser beam hand pieced. Accordingly, the entire length or size of the optical means is generally increased and alignment of the laser beam may be changed due to heat of the laser beam.

DISCLOSURE

Technical Problem

An embodiment of the present invention provides a laser beam device and a laser beam hand piece having the same having a compact structure capable of outputting a polarized laser beam.

Furthermore, an embodiment of the present invention provides a laser beam device and a laser beam hand piece having the same capable of outputting a laser beam of a wavelength band and output energy according to a cure purpose.

Technical Solution

In accordance with an aspect of the present invention, there is provided a laser beam device including: a light source unit emitting a pumping light; a first optical unit generating a laser beam that is polarized by being pumped by the pumping light provided from the light source unit; and a second optical unit amplifying the polarized laser beam provided from the first optical unit.

The second optical unit may be disposed between the light source unit and the first optical unit, and a focus of the pumping light emitted from the light source unit may be formed inside the first optical unit.

The pumping light emitted from the light source unit may be partially absorbed in the second optical unit and may be focused in the first optical unit according to a location of the focus.

The pumping light emitted from the light source unit may be absorbed relatively more than the second optical unit by the first optical unit.

A first wavelength pumping light emitted from the light source unit may be generated by the first optical unit and the second optical unit.

An input surface of the second optical unit to which the first wavelength pumping light is input may have a transmittance higher than the first wavelength pumping light and a reflectivity higher than the second wavelength laser beam.

The laser beam device may further include a third optical unit disposed oppositely to the second optical unit while interposing the first optical unit 320 therebetween to resonate a laser beam so that the laser beam is oscillated from the laser beam device.

The laser beam device may further include a fourth optical unit disposed between the first optical unit and the third optical unit to switch a pulse width of a laser beam resonating between the second optical unit and the third optical unit as a relatively short pulse width.

The first optical unit and the fourth optical unit may be anti-refection coated.

The first optical unit and the second optical unit may include Nd:YVO4 and Nd:YAG, respectively.

The fourth optical unit may be configured by a Q-switcher.

A wavelength band of a laser beam generated from the first optical unit may be similar to a wavelength band of a laser beam generated from the second optical unit.

The first optical unit may have a pumping optical absorption characteristic having a high absorption rate with respect to a pumping light as compared with the second optical unit.

The first optical unit may be disposed between the light source unit and the second optical unit and may oscillate a laser beam which is polarized and amplified by being pumped by the pumping light provided from the light source unit.

The first optical unit may have a pumping optical absorption characteristic having a high absorption rate with respect to a pumping light as compared with the second optical unit.

A wavelength band of a laser beam generated from the first optical unit may be similar to a wavelength band of a laser beam generated from the second optical unit.

The first optical unit and the second optical unit may include Nd:YV04 and Nd:YAG, respectively.

In accordance with another aspect of the present invention, there is provided a laser beam hand piece including: a hand piece; and the laser beam device outputting a polarized laser beam to an outside of the hand piece.

The details of other embodiments are contained in the detailed description and accompanying drawings.

Advantageous Effects

The laser beam device and the laser beam hand piece having the same according to the present invention have advantages as follows.

First, a compact structure and the outputting of a polarized laser beam having amplified output energy may be enabled, and thus the size and manufacturing costs of the laser beam device and the laser beam hand piece having same may be reduced.

Second, since a fourth optical unit is further disposed so that output energy is increased and a polarized laser beam may be switched, usability of the product may be increased by outputting a laser beam having a relatively short pulse width.

MODE FOR INVENTION

Figure 1:
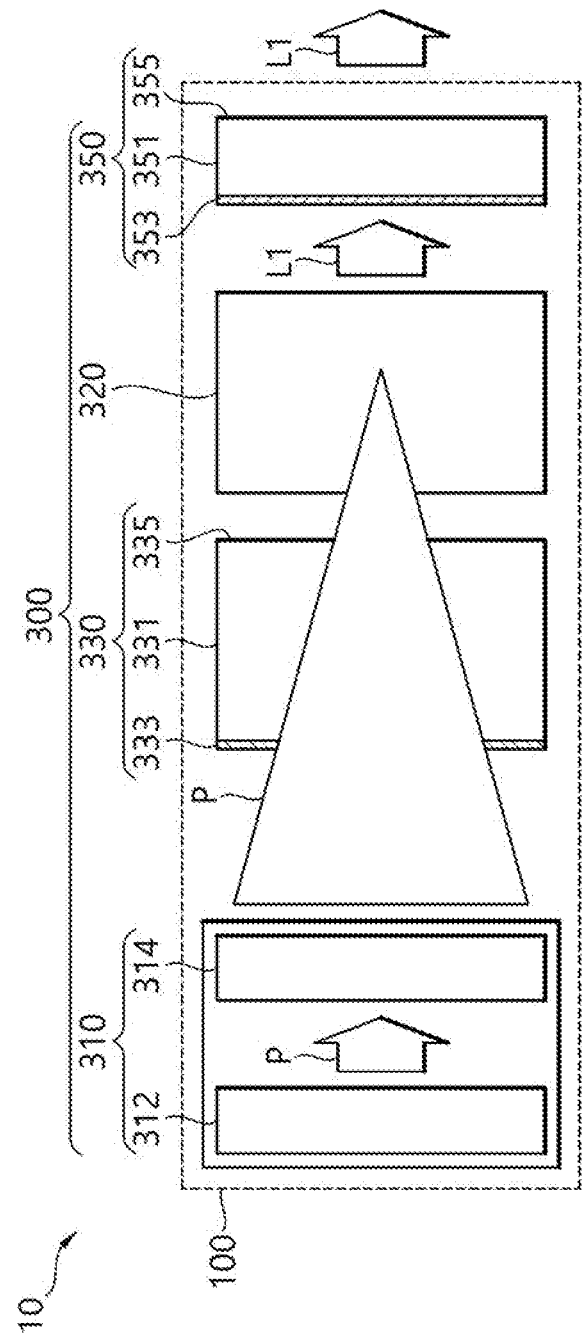
FIG. 1 is a schematic view illustrating a configuration of a laser beam hand piece according to a first embodiment of the present invention.

Hereinafter, a laser beam device and a laser beam handle piece having the same according to the exemplary embodiment of the present invention will be described with reference to the accompanying drawings.

Before the description, although the laser beam device according to the present invention is described to be used in the laser beam hand piece, the laser beam device may be applied to various devices or systems in addition to the laser beam hand piece.

The similar components will be assigned with the similar reference numerals through the specification in the laser beam device and the laser beam hand piece having the same according to first to third embodiments of the present invention.

Further, since a pulse width of a second wavelength laser beam L2 according to a second embodiment of the present invention differs from a pulse width of a first wavelength laser beam L1 according to a first embodiment of the present invention, the first wavelength laser beam L1 and the second wavelength laser beam L2 will be assigned with different reference numerals.

Meanwhile, although a second wavelength laser beam L1 is oscillated in a third embodiment of the present invention, a second wavelength laser beam L2 may be oscillated by adding a fourth optical unit of a second embodiment.

First Embodiment

Figure 2:
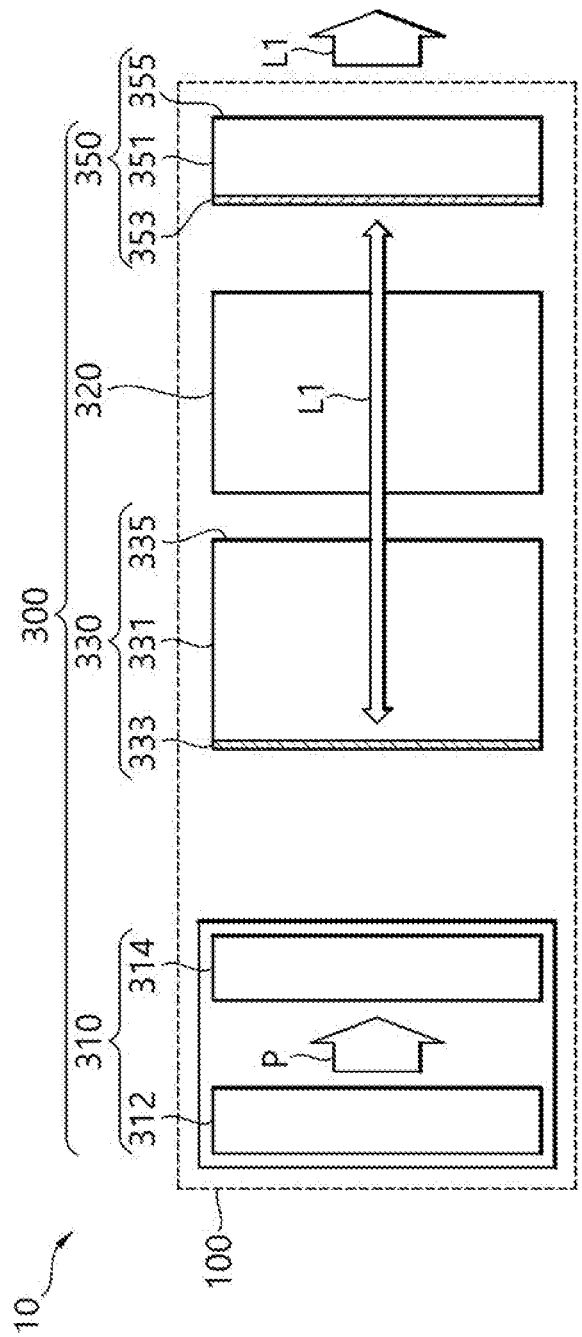
FIG. 2 is a schematic view illustrating a laser beam resonance configuration of a laser beam hand piece according to a first embodiment of the present invention.

FIG. 1 is a schematic view illustrating a configuration of a laser beam hand piece according to a first embodiment of the present invention and FIG. 2 is a schematic view illustrating a laser beam resonance configuration of a laser beam hand piece according to a first embodiment of the present invention.

As shown in FIG. 1 and FIG. 2, a laser beam hand piece 10 according to a first embodiment of the present invention include a hand piece 100 and a laser beam device 300. The hand piece 100 is received in the laser beam device 300 and is gripped by a practitioner. The hand piece 100 may has various shaped such as a hopper a section of which is gradually reduced from an upstream to a downstream or a barrel shape having a constant section.

A laser beam device 300 of a laser beam hand piece 10 according to a first embodiment of the present invention includes a light source unit 310, a first optical unit 320, and a second optical unit 330. The laser beam device 300 of a laser beam hand piece 10 according to a first embodiment of the present invention further includes a third optical unit 350. The laser beam device 300 according to an embodiment of the present invention a light source unit 310 emitting a pumping light; a first optical unit 320 generating a laser beam that is polarized by being pumped by the pumping light provided from the light source unit; and a second optical unit 330 amplifying the polarized laser beam provided from the first optical unit. Here, although the light source unit 310, the second optical unit 330, and the first optical unit 320 are disposed in the order of the light source unit 310, the second optical unit 330, and the first optical unit 320 according to an emission direction of a pumping light in the first embodiment of the present invention, the disposal order of the first optical unit 320 the second optical unit 330 may be changed. If the disposal order of the first optical unit 320 the second optical unit 330 is changed, that is, if the light source unit 310, the first optical unit 320, and the second optical unit 330 are disposed in the order of the light source unit 310, the first optical unit 320, and the second optical unit 330, a lens 314 of the light source unit 310 to be described below may be omitted.

The light source unit 310 generates and emits a pumping light into the hand piece 100. The light source unit 310 is configured by an optical fiber or a laser diode (LD) array connected to one side of the hand piece 100 as an example of the present invention. The light source unit 310 may use various types of light sources to generate and emit a pumping light in addition to the optical fiber or the LD array.

The light source unit 310 includes a light source 312 and a lens 314. The light source 312 emits a first wavelength pumping light P. As an embodiment of the present invention, the first wavelength pumping light P emitted from the light source 312 has a wavelength of 808 nm. Further, the first wavelength pumping light P emitted from the light source 312 has a micro-second pulse width as an example. Here, a wavelength and a pulse width of the first wavelength pumping light P emitted from the light source 312 is not limited to 808 nm and micro-second unit, respectively, but may be selectively changed.

The lens 314 focuses the pumping light provided from the light source 312 in a first optical unit 320. The lens 314 has a convex shape to form a focus of the pumping light provided from the light source 310 into the first optical unit 320. A shape of the lens 314 is not limited to the shape of a convex lens, and various lenses capable of forming a focus of the pumping light provided from the light source 312 in the first optical unit 320 can be used.

The first optical unit 320 generates a laser beam that is polarized by being pumped by the pumping light provided from the light source unit 310. The first optical unit 320 includes Nd:YV04 as an example. Since the first optical unit 320 configured by Nd:YV04 has an absorption rate with respect to the pumping light being a pumping light absorption characteristic of about five times better than the second light source unit 300 configured by Nd:YAG to be described below, the overall device may be compactly configured. In addition, the first optical unit 320 has a wavelength absorption band wider than that of the second optical unit 330. In particular, the first optical unit 320 generates a laser beam that is polarized by being pumped by the input pumping light. The first optical unit 320 essentially generates a second wavelength laser beam L1 that is polarized by being pumped by a first wavelength pumping light provided from the light source unit 310.

As described above, the first optical unit 320 may generate the laser beam that is polarized by being pumped by the incident pumping light so that the laser beam device 300 according to the present invention to output a polarized laser beam without a polarizing means such as a polarizer. Here, the first optical unit 320 is anti-refection coated so that a laser beam may resonate between a second input surface 333 of the second optical unit 330 and a third input surface 353 of the third optical unit 350.

The second optical unit 330 amplifies the polarized laser beam provided from the first optical unit 320. In detail, the second optical unit 330 amplifies output energy of the polarized laser beam when the polarized laser beam generated from the first optical unit 320 is reflected and provided by the third optical unit 350. The second optical unit 330 generates a laser beam of output energy higher than that of the laser beam generated from the first optical unit 320. The second optical unit 330 uses Nd:YAG in order to amplify output energy of the polarized laser beam provided from the first optical unit 320. However, the second optical unit 330 may use an optical crystal having a similar optical characteristic in addition to Nd:YAG.

The second optical unit 330 includes a second body 331, a second input surface 333, and a second output surface 335. The second input surface 333 is provided to have a transmittance higher than that of the first wavelength pumping light P provided from the light source unit 310 and a reflectivity higher than that of the second wavelength laser beam L1. That is, the second wavelength laser beam L1 resonates between the second input surface 333 of the second optical unit 330 and the third input surface 353 of the third optical unit 350 to be described below to oscillate through the third optical unit 350.

Meanwhile, a wavelength band of a laser beam generated from the first optical unit 320 is similar to a wavelength band of a laser beam generated from the second optical unit 330. That is, the laser beams from the first optical unit 320 and the second optical unit 330 are generated as the second wavelength laser beam L1, and the second wavelength laser beam L1 has a wavelength band of 1064 nm. A wavelength of each laser beam generated from the first optical unit 320 and the second optical unit 330 may have various wavelength bands in addition to a wavelength band of 1064 nm.

A focus of the pumping light emitted from the light source unit 310 is formed inside the first optical unit 320. That is, the pumping light emitted from the light source 312 of the light source unit 310 is formed inside the first optical unit 320 by the lens 314. The pumping light emitted from the light source 314 is partially absorbed in the second optical unit 330 according to a location of a focus by the lens 314 and is focused in the first optical unit 320. The pumping light emitted from the light source unit 310 is absorbed in the first optical unit 320 more than the second optical unit 330. That is, the first optical unit 320 has a pumping optical absorption characteristic having a high absorption rate with respect to a pumping light as compared with the second optical unit 330.

If a pumping optical absorption characteristic of the first optical unit 320 and the second optical unit 330 is considered, since the first optical unit has a higher absorption rate with respect to the pumping light as compared with the second optical unit, a pumping light not absorbed in the first optical unit 330 is absorbed in the first optical unit 320 to be polarized and the second wavelength laser beam L1 having amplified output energy oscillates. In this case, as described above, it is preferred to maintain a threshold oscillation value so that a density of the pumping light from the second optical unit 330 is low in the second optical unit 300 or achieve a density so that oscillation of a higher degree is achieved by forming a focus of the pumping light P inside the first optical unit 320. When the above condition is satisfied, the polarized second wavelength laser beam generated from the first optical unit 320 is outputted as the polarized second wavelength laser beam L1 having a relatively increased output energy because the second optical unit 330 functions as an amplifier.

Next, the third optical unit 350 is disposed oppositely to the second optical unit 330 while interposing the first optical unit 320 therebetween. The third optical unit 350 resonates the second wavelength laser beam L1 between the second optical unit 330 and the third optical unit 350. The third optical unit 350 includes a third body 351, a third input surface 353, and a third output surface 355.

The third input surface 353 resonates the second wavelength laser beam L1 partially reflected with respect to the second wavelength laser beam L1 between the second input surface 333 of the second optical unit 330 and the third input surface 353. Moreover, the third output surface 355 is anti-refection coated with respect to the second wavelength laser beam L1.

An operation of the laser beam hand piece 10 according to the first embodiment of the present invention is as follows by the above configuration.

The light source unit 310 emits a first wavelength pumping light P into a hand piece 100. A focus of the first wavelength pumping light P provided from the light source 312 is formed inside the first optical unit 320 by the lens 314. Accordingly, a part of the first wavelength pumping light P is absorbed as the pumping light in the second optical unit 330, and remaining pumping light is absorbed in the first optical unit 320.

The first optical unit 320 generates a laser beam that is polarized by being pumped by the pumping light provided from the light source unit 310, and a second optical unit 330 amplifies the polarized laser beam provided from the first optical unit 320. That is, the polarized second wavelength laser beam L1 generated from the first optical unit 320 resonates between the second input surface 333 of the second optical unit 330 and the third input surface 353 of the third optical unit 350 so that output energy is amplified and the second wavelength laser beam L1 oscillates to the second output surface 355 of the third optical unit 350.

Second Embodiment

Figure 3:
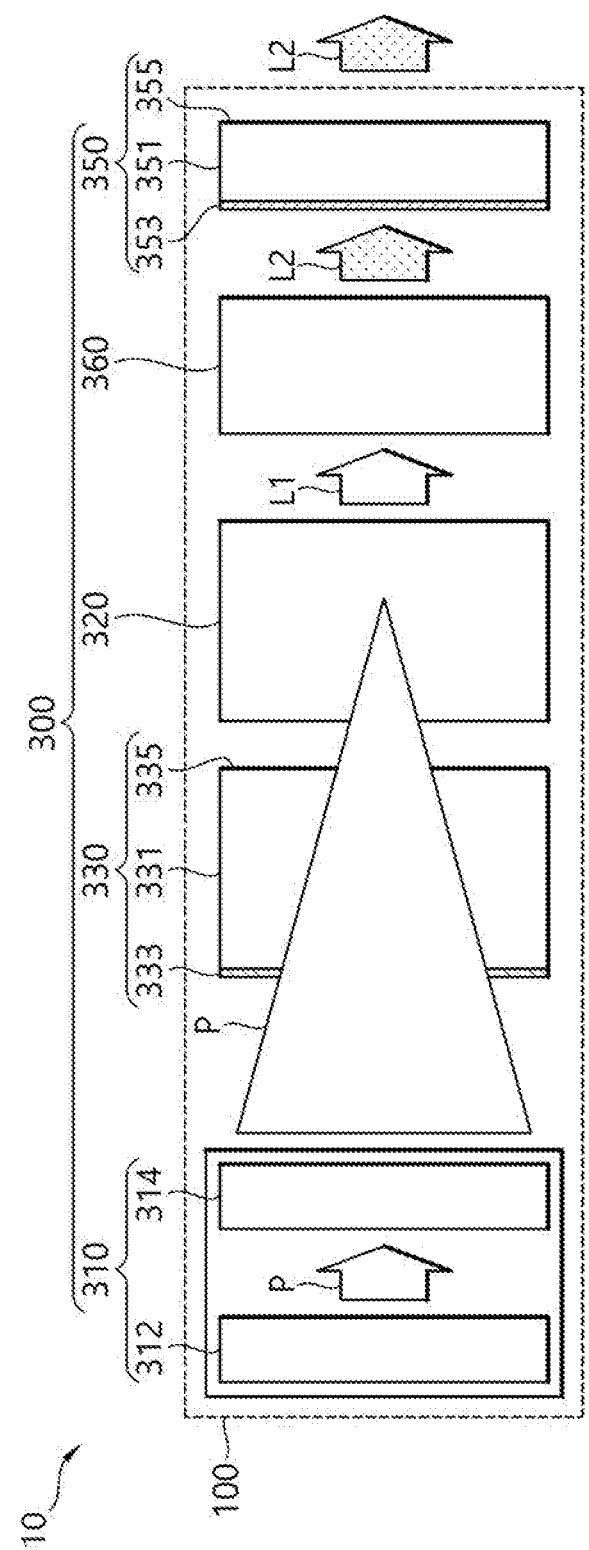
FIG. 3 is a schematic view illustrating a configuration of a laser beam hand piece according to a second embodiment of the present invention.
Figure 4:
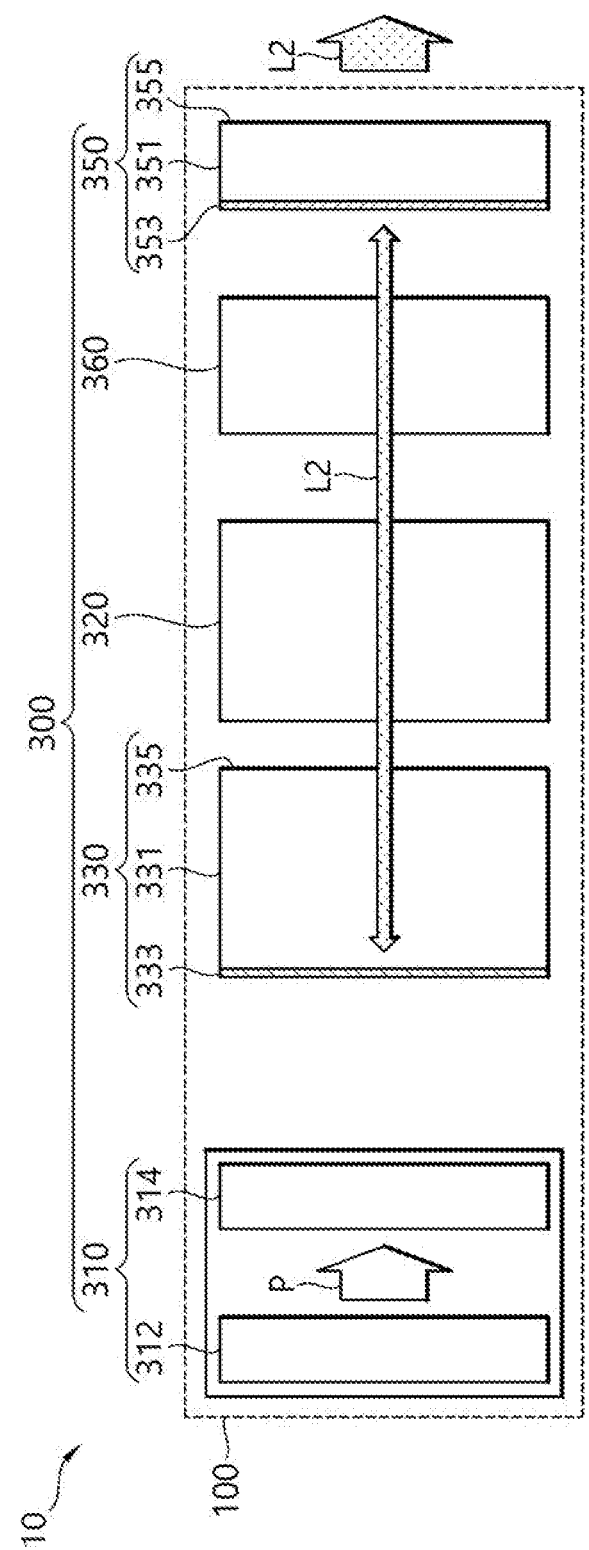
FIG. 4 is a schematic view illustrating a laser beam resonance configuration of a laser beam hand piece according to a second embodiment of the present invention.

FIG. 3 is a schematic view illustrating a configuration of a laser beam hand piece according to a second embodiment of the present invention, and FIG. 4 is a schematic view illustrating a laser beam resonance configuration of a laser beam hand piece according to a second embodiment of the present invention.

As shown in FIG. 3 and FIG. 4, the laser beam hand piece 10 according to the second embodiment of the present invention include a hand piece 100 and a laser beam device 300. A laser beam device 300 of a laser beam hand piece 10 according to a second embodiment of the present invention includes a light source unit 310, a first optical unit 320, a second optical unit 330, a third optical unit 350 and a fourth optical unit 360. The laser beam hand piece 10 according to a second embodiment of the present invention further includes a fourth optical unit 360 as compared with the first embodiment. The light source unit 310, the first optical unit 320, the second optical unit 330, and a first optical unit 350 are the same as those of the first embodiment, and thus the detailed description thereof is appropriately omitted.

The fourth optical unit 360 is disposed between the first optical unit 320 and the third optical unit 350. The fourth optical unit 360 switches the second wavelength laser beam L2 to a second wavelength laser beam L2 so that a pulse width of the second wavelength laser beam L1 resonating between the second optical unit 330 and the third optical unit 350 has a relatively short pulse width. As an embodiment of the present invention, the fourth optical unit 360 switches the second wavelength laser beam L1 having a micro-second pulse width to the second wavelength laser beam L2 having several pico-second (ps) to several hundreds nano-second (ns) pulse width. As an embodiment of the present invention, the second wavelength laser beam L1 having a micro-second unit becomes a second wavelength laser beam L2 having a pico-second to nano-second unit by the fourth optical unit 360.

The fourth optical unit 360 is configured by a Q-switcher and includes Cr:YAG as an example. Although the above embodiment has described that the fourth optical unit 360 uses a passive Q-switcher such as Cr:YAG as an example of the present invention, an active Q-switcher such as a pockels cell may be used. The fourth optical unit 360 using the Cr:YAG is illustrative purpose only and various optical crystals for switching the second wavelength laser beam L1 to a relatively short pulse width may be used. As in the first optical unit 320, the fourth optical unit 360 is anti-refection coated so that a laser beam may resonate between the second input surface 333 of the second optical unit 330 and the third input surface 353 of the fourth optical unit 350.

An operation of the laser beam hand piece 10 according to the second embodiment of the present invention is as follows by the above configuration.

The light source unit 310 emits a first wavelength pumping light P into the hand piece 100. A focus of the first wavelength pumping light P provided from the light source 312 is formed inside the first optical unit 320. Accordingly, a part of the first wavelength pumping light P is absorbed as the pumping light in the second optical unit 330, and remaining pumping light is absorbed in the first optical unit 320.

The first optical unit 320 generates a laser beam that is polarized by being pumped by the pumping light provided from the light source unit 310. The second optical unit 330 amplifies the polarized laser beam provided from the first optical unit 320. The second wavelength laser beam L1 is provided to the fourth optical unit 360. The fourth optical unit 360 switches a pulse width of the second wavelength laser beam L1 to a second wavelength laser beam L2 having a relatively short pulse width.

Third Embodiment

Figure 5:
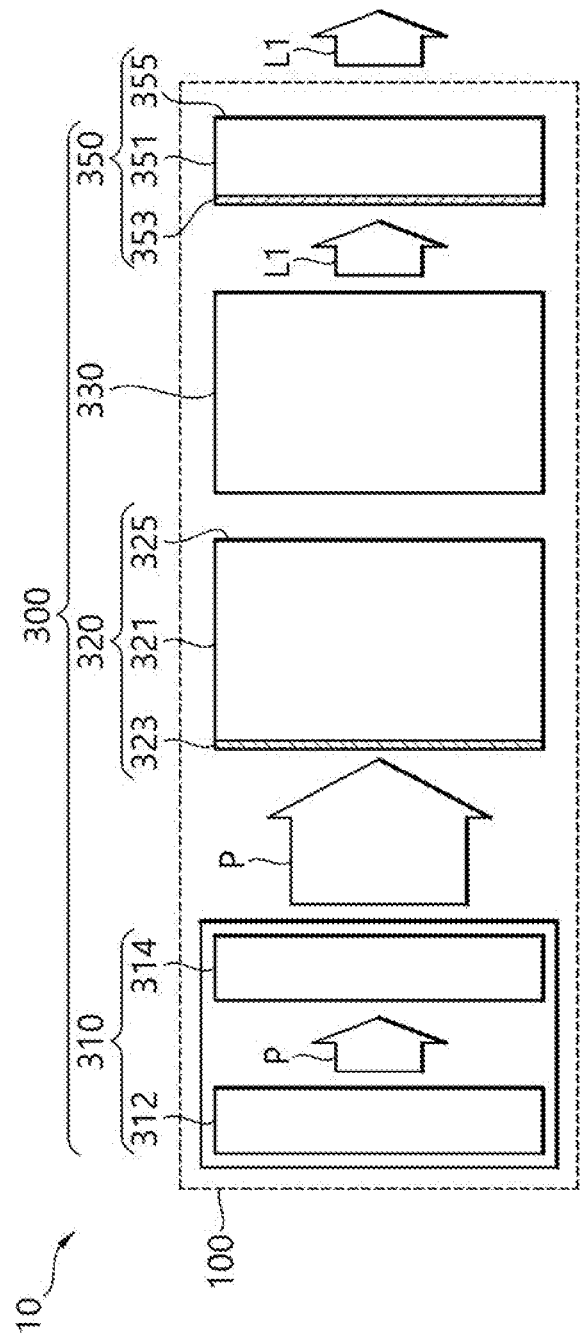
FIG. 5 is a schematic view illustrating a laser beam resonance configuration of a laser beam hand piece according to a third embodiment of the present invention.
Figure 6:
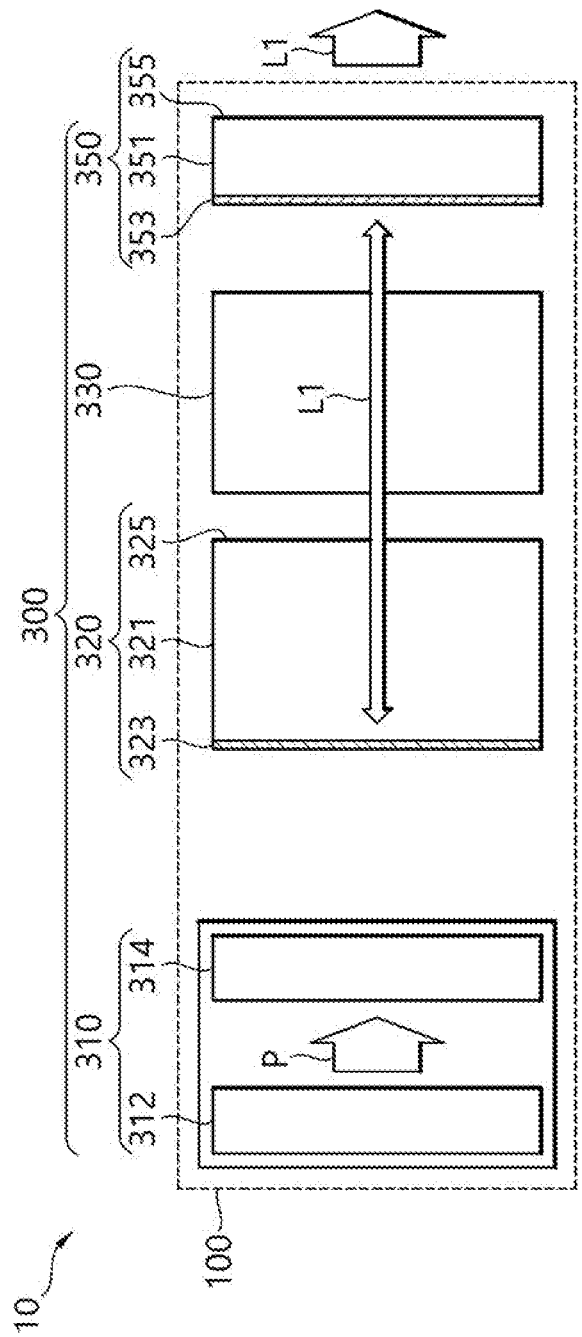
FIG. 6 is a schematic view illustrating a laser beam resonance configuration of a laser beam hand piece according to a third embodiment of the present invention.

FIG. 5 is a schematic view illustrating a laser beam resonance configuration of a laser beam hand piece according to a third embodiment of the present invention, and FIG. 6 is a schematic view illustrating a laser beam resonance configuration of a laser beam hand piece according to a third embodiment of the present invention.

As shown in FIG. 5 and FIG. 6, the laser beam hand piece according to the third embodiment of the present invention include a hand piece 100 and a laser beam device 300. A laser beam device 300 of a laser beam hand piece 10 according to a third embodiment of the present invention includes a light source unit 310, a first optical unit 320, and a second optical unit 330. The laser beam device 300 according to the third embodiment of the present invention further includes a third optical unit 350.

The laser beam device 300 according to the third embodiment of the present invention includes a light source unit 310 emitting a pumping light, a first optical unit 320 generating a laser beam that is polarized by being pumped by the pumping light provided from the light source unit 310, and a second optical unit 330 amplifies the polarized laser beam provided from the first optical unit 320. Here, in the third embodiment of the present invention, the light source unit 310, the first optical unit 320, and the second optical unit 330 are disposed in the order of the light source unit 310, the first optical unit 320, and the second optical unit 330 according to an emission direction of the pumping light. That is, unlike the first embodiment of the present invention, the locations of the first optical unit 320, and the second optical unit 330 are changed to each other in the third embodiment of the present invention.

According to disposal locations of the first optical unit 320, and the second optical unit 330, the light source unit 310 of the third embodiment of the present invention does not need an optical structure for forming a focus inside the first optical unit unlike the first embodiment of the present invention.

The first optical unit 320 generates a laser beam that is polarized by being pumped by the pumping light provided from the light source unit 310. The first optical unit 320 includes Nd:YVO4 as an example. Since the first optical unit 320 configured by Nd:YVO4 has an absorption rate with respect to the pumping light being a pumping light absorption characteristic of about five times better than the second light source unit 300 configured by Nd:YAG to be described below, the overall device may be compactly configured. In addition, the first optical unit 320 has a wavelength absorption band wider than that of the second optical unit 330. In particular, the first optical unit 320 generates a laser beam that is polarized by being pumped by the incident pumping light. The first optical unit 320 essentially generates a second wavelength laser beam L1 that is polarized by being pumped by a first wavelength pumping light provided from the light source unit 310.

As described above, the first optical unit 320 generates the laser beam that is polarized by being pumped by the incident pumping light so that the laser beam device 300 according to the present invention may output a polarized laser beam without a polarizing means such as a polarizer. Here, the first optical unit 320 includes a first body 321, a first input surface 323, and a first output surface 325. The first input surface 323 is provided to have a transmittance higher than the first wavelength pumping light P provided from the light source unit 310 and a reflectivity higher than the second wavelength laser beam L1. That is, the second wavelength laser beam L1 resonates between the first input surface 323 of the first optical unit 320 and the third input surface 353 of the third optical unit 350 to be described below and oscillates through the third optical unit 350.

The second optical unit 330 amplifies the polarized laser beam provided from the first optical unit 320. The second optical unit 330 generates a laser beam of output energy higher than that of the laser beam generated from the first optical unit 320. The second optical unit 330 uses Nd:YAG in order to amplify output energy of the polarized laser beam provided from the first optical unit 320. However, the second optical unit 330 may use an optical crystal having a similar optical characteristic in addition to Nd:YAG. Here, the second optical unit 330 is anti-refection coated so that a laser beam may resonate between a first input surface 323 of the first optical unit 320 and a third input surface 353 of the third optical unit 350.

Meanwhile, a wavelength band of a laser beam generated from the first optical unit 320 is similar to a wavelength band of a laser beam generated from the second optical unit 330. That is, the laser beams from the first optical unit 320 and the second optical unit 330 are generated as the second wavelength laser beam L1, and the second wavelength laser beam L1 has a wavelength band of 1064 nm. A wavelength of each laser beam generated from the first optical unit 320 and the second optical unit 330 may have various wavelength bands in addition to a wavelength band of 1064 nm.

Next, the third optical unit 350 is disposed oppositely to the second optical unit 330 while interposing the first optical unit 320 therebetween. The third optical unit 350 resonates the second wavelength laser beam L1 between the second optical unit 330 and the third optical unit 350. The third optical unit 350 includes a third body 351, a third input surface 353, and a third output surface 355.

The third input surface 353 resonates the second wavelength laser beam L1 partially reflected with respect to the second wavelength laser beam L1 between the second input surface 333 of the second optical unit 330 and the third input surface 353. Moreover, the third output surface 355 is anti-refection coated with respect to the second wavelength laser beam L1.

An operation of the laser beam hand piece 10 according to the third embodiment of the present invention is as follows by the above configuration.

The light source unit 310 emits a first wavelength pumping light P into a hand piece 100. The first optical unit 320 generates a laser beam that is polarized by being pumped by the pumping light provided from the light source unit 310, and a second optical unit 330 amplifies the polarized laser beam provided from the first optical unit 320. That is, the polarized second wavelength laser beam L1 generated from the first optical unit 320 resonates between the first input surface 323 of the first optical unit 320 and the third input surface 353 of the third optical unit 350 so that output energy is amplified and the second wavelength laser beam L1 oscillates to the second output surface 355 of the third optical unit 350.

INDUSTRIAL APPLICABILITY

A compact structure and the outputting of a polarized laser beam having amplified output energy may be enabled, and thus the size and manufacturing costs of the laser beam device and the laser beam hand piece having same may be reduced.

Since a fourth optical unit is further disposed so that output energy is increased and a polarized laser beam may be switched, usability of the product may be increased by outputting a laser beam having a relatively short pulse width.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

The invention claimed is:

1. A laser beam device comprising:
a light source unit configured to emit a pumping light;
a first optical unit configured to generate a laser beam that is polarized by being pumped by the pumping light provided from the light source unit;
a second optical unit configured to amplify the polarized laser beam provided from the first optical unit; and
a third optical unit provided oppositely to the second optical unit while interposing the first optical unit therebetween,
wherein the first optical unit absorbs the pumping light emitted from the light source unit more than the second optical unit, and
wherein the laser beam is resonated between reflective surfaces respectively provided in the second optical unit and the third optical unit, and the entire second optical unit is provided within a resonant path of the laser beam.

2. The laser beam device of claim 1, wherein a focus of the pumping light emitted from the light source unit is formed inside the first optical unit.

3. The laser beam device of claim 2, wherein the pumping light emitted from the light source unit is partially absorbed in the second optical unit and is focused in the first optical unit according to a location of the focus.

4. The laser beam device of claim 2, wherein a first wavelength pumping light emitted from the light source unit is generated by the first optical unit and the second optical unit.

5. The laser beam device of claim 4, wherein an input surface of the second optical unit to which the first wavelength pumping light is input has a transmittance higher than that of the first wavelength pumping light and a reflectivity higher than that of the second wavelength laser beam.

6. The laser beam device of claim 2, further comprising a fourth optical unit disposed between the first optical unit and the third optical unit to switch a pulse width of a laser beam resonating between the second optical unit and the third optical unit as a relatively short pulse width.

7. The laser beam device of claim 6, wherein the first optical unit and the fourth optical unit are anti-refection coated.

8. The laser beam device of claim 2, wherein the first optical unit and the second optical unit comprise Nd:YVO$_4$ and Nd:YAG crystals, respectively.

9. The laser beam device of claim 6, wherein the fourth optical unit is configured by a Q-switcher.

10. The laser beam device of claim 2, wherein a wavelength band of a laser beam generated from the first optical unit is similar to a wavelength band of a laser beam generated from the second optical unit.

11. The laser beam device of claim 8, wherein the first optical unit has a pumping optical absorption characteristic having a high absorption rate with respect to a pumping light as compared with the second optical unit.

12. The laser beam device of claim 1, wherein the first optical unit is disposed between the light source unit and the second optical unit and oscillates a laser beam which is polarized and amplified by being pumped by the pumping light provided from the light source unit.

13. The laser beam device of claim 12, wherein the first optical unit has a pumping optical absorption characteristic having a high absorption rate with respect to a pumping light as compared with the second optical unit.

14. The laser beam device of claim 12, wherein a wavelength band of a laser beam generated from the first optical unit is similar to a wavelength band of a laser beam generated from the second optical unit.

15. The laser beam device of claim 12, wherein the first optical unit and the second optical unit comprise Nd:YVO$_4$ and Nd:YAG crystals, respectively.

16. A laser beam hand piece comprising:
a hand piece; and
a laser beam device according to claim 1 outputting a polarized laser beam to an outside of the hand piece.

17. A laser beam device comprising:
a light source unit configured to emit a pumping light;
a first optical unit configured to generate a laser beam that is polarized by being pumped by the pumping light provided from the light source unit; and
a second optical unit provided between the light source unit and the first optical unit,
wherein the first optical unit absorbs the pumping light emitted from the light source unit more than the second optical unit, and
wherein the laser beam is resonated between reflective surfaces, and the entire second optical unit is provided within a resonant path of the laser beam and amplifies the laser beam.

18. The laser beam device of claim 1, wherein the entire second optical unit is provided between the light source unit and the first optical unit.

* * * * *